United States Patent
Vite et al.

(10) Patent No.: US 6,380,395 B1
(45) Date of Patent: Apr. 30, 2002

(54) 12, 13-CYCLOPROPANE EPOTHILONE DERIVATIVES

(75) Inventors: Gregory D. Vite, Titusville; Soong-Hoon Kim, Lawrenceville, both of NJ (US); Gerhard Höfle, Braunschweig (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/280,192

(22) Filed: Mar. 29, 1999

Related U.S. Application Data

(60) Provisional application No. 60/082,564, filed on Apr. 21, 1998.

(51) Int. Cl.$^7$ .................. C07D 277/04; C07H 17/08
(52) U.S. Cl. .............................. 548/146; 536/7.1
(58) Field of Search ................... 536/7.1; 548/146

(56) References Cited

U.S. PATENT DOCUMENTS

| | | |
|---|---|---|
| 6,194,181 B1 | 2/2001 | Hofmann et al. |
| 6,204,388 B1 | 3/2001 | Danishefsky et al. |
| 6,211,412 B1 | 4/2001 | Georg et al. |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | WO 9822461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | WO 99/39694 | 8/1999 |
| WO | WO 9942602 | 8/1999 |
| WO | WO 9943320 | 9/1999 |
| WO | WO 99/43653 | 9/1999 |
| WO | WO 99/67252 | 12/1999 |
| WO | WO 00/00485 | 1/2000 |
| WO | WO 0031247 | 6/2000 |
| WO | WO 00/37473 | 6/2000 |
| WO | WO 00/49021 | 8/2000 |
| WO | WO 00/66589 | 11/2000 |

OTHER PUBLICATIONS

Nicolaou et al, "Synthesis and Biological Properties of C 12, 13–Cyclopropylepothiolone A and Related Epothilones", Chemistry & Biology, vol. 5, No. 7, pp. 365–372 (Jun. 1998).*

Nicolaou et al, "Total Synthesis of Oxazole– and Cyclopropane–Containing Epothilone A Analogues by the Olefin Metathesis Approach", Chem. Eur. J., vol. 3, No. 12, pp. 1957–1970 (1997).*

Altmann et al., 2000, "Epothilones and Related Structures—A New Class of Microtubule Inhibitors with Potent In Vivo Antitumor Activity", Biochim. Biophys. Acta, 1470:M79–M91.

Nicolaou et al., 1998, "Total Synthesis of Epothilone E and Analogs with Modified Side Chains Through the Stille Coupling Reaction", Angew. Chem. Int. Ed. 37: 84–87.

Nicolaou et al., 1998, "Chemistry and Biology of Epothilones", Angew. Chem. Int. Ed. 37:2014–2045.

Balog, A., et al., "Total Synthesis of (–)–Epothilone A", Angew. Chem. Int. Ed. Engl., vol. 35, No. 23/24, 2801–2803 (1996).

Bertini, F., et al., "Alkenes from Epoxides by Reductive Elimination with Magnesium Bromide–Magnesium Amalgam", Chem. Commun. , 144 (1970).

Bollag, D.M., et al., "Epothilones, A New Class of Microtubule–stabilizing Agents with a Taxol–like Mechanism of Action", Cancer Res. 55, No. 11, 2325–2333 (1995).

Fujisawa, T., et al., "Deoxygenation of Epoxides to Olefins with $FeCl_3$—n–BuLi System", Chem. Lett., 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", J. Org. Chem., vol. 43, No. 12, 2477–2479 (1978).

Gladysz, J. A., et al., "Deoxygenation of Epoxides by Metal Atom Cocondensation", J. Org. Chem., vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", Angew. Chem. Int. Ed. Engl., vol. 35, No. 13/14, 1567–1569 (1996).

Hofle, G., et al., "N–Oxidation of Epothilone A–C and O–Acyl Rearrangement to C–19 and C–21 –Substituted Epothilones", Angew. Chem. Int. Ed., vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", Synlett, No. 6, 510–512 (1992).

(List continued on next page.)

Primary Examiner—James O. Wilson
Assistant Examiner—Everett White
(74) Attorney, Agent, or Firm—Rena Patel; Joan Switzer

(57) ABSTRACT

The present invention relates to 12,13-position modified epothilone derivatives, methods of preparation of the derivatives and intermediates therefor.

22 Claims, No Drawings

OTHER PUBLICATIONS

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low-Valent Titanium ($TiCl_3/LiAlH_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et. al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5/NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and—Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothiolone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1 / 2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)–Epothilone A", *Chem. Eur. J.*, vol. 5, No. 9, 2483–2491 (1999).

Schinzer, D., et al., "Syntheses of (–)–Epothilone B", *Chem. Eur. J.*, vol. 5, No. 9, 2492–2500 (1999).

Nicolaou, K. C., et al., "Synthesis and Biological Properties of C12,13–Cyclopropylepothilone A and Related Epothilones", *Chemistry & Biology*, vol. 5, No. 7, 365–372 (1998).

* cited by examiner

12,13-CYCLOPROPANE EPOTHILONE DERIVATIVES

This application claims priority to provisional application no. 60/082,564, filed Apr. 21, 1998, which is hereby incorporated by reference in its entirety.

The present invention relates to compounds of the formula

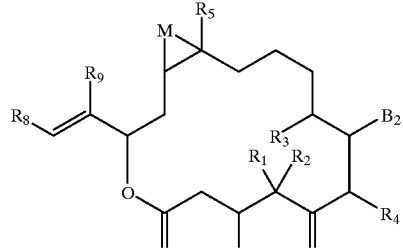

I

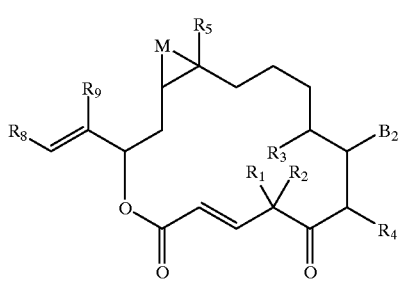

II $B_1$ and $B_2$ are selected from the group consisting of H, or $OR_6$;

$R_1$, $R_2$, $R_3$, and $R_4$, are selected from H, lower alkyl;

$R_5$ is selected from the group consisting of H, alkyl, substituted alkyl;

$R_8$ is heterocyclo;

$R_9$ is hydrogen or lower alkyl;

$R_6$, is hydrogen or alkyl;

M is $CR_{10}R_{11}$.

$R_{10}$ and $R_{11}$ are selected from the group consisting of H, halogen, alkyl, substituted alkyl, aryl, substituted aryl, cycloalkyl, heterocyclo, $R_{12}C=O$, $R_{13}OC=O$, $R_{14}NHC=O$, hydroxy, O-alkyl or O-substituted alkyl, $NR_{15}R_{16}$;

$R_{12}$, $R_{13}$, $R_{14}$, $R_{15}$, $R_{17}$, $R_{18}$ and $R_{19}$ are selected from the group consisting of H, alkyl, substituted alkyl, aryl, acyl or substituted aryl.

$R_{16}$ is selected from the group consisting of H, alkyl, substituted alkyl, aryl, substituted aryl, cycloalkyl, heterocyclo, $R_{17}C=O$, $R_{18}OC=O$, $R_{19}SO_2$, hydroxy, O-alkyl, or O-substituted alkyl and any salts, solvates or hydrates thereof.

BACKGROUND OF THE INVENTION

Epothilones are macrolide compounds which find utility in the pharmaceutical field. For example, Epothilones A and B having the structures:

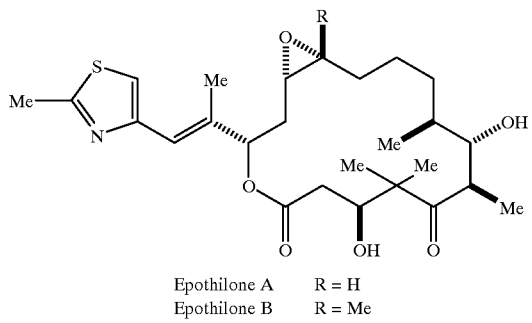

Epothilone A  R = H
Epothilone B  R = Me have been found to exert microtubule-stabilizing effects similar to TAXOL and hence cytotoxic activity against rapidly proliferating cells, such as, tumor cells or other hyperproliferative cellular disease, see Angew. Chem. Int. Ed. Engl., 1996, 35, No. 13/14.

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, phenyl, substituted phenyl, heterocyclo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio; heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I and II may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be obtained, for example, by exchanging the carboxylic acid protons, if they contain a carboxylic acid, in compounds of formula I and II with the desired ion in a medium in which the salt precipitates or in an aqueous medium followed by evaporation. Other salts can be formed as known to those skilled in the art.

The compounds for formula I and II form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound of formula I and II in an equivalent amount of the acid in a medium in which the salt precipitates or in an aqueous medium followed by evaporation.

In addition, zwitterions ("inner salts") are formed.

Compounds of the formula I and II may also have prodrug forms. Any compound that will be converted in vivo to provide the bioactive agent (i.e., the compound for formula I and II) is a prodrug within the scope and spirit of the invention.

For example compounds of the formula I and II may form a carboxylate ester moiety. The carboxylate esters are conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77, 285 (1988); and e) N. Kakeya, et al., *Chem Phar Bull*, 32, 692 (1984).

It should further be understood that solvates (e.g., hydrates) of the compounds of formula I and II are also within the scope of the present invention. Methods of solvation are generally known in the art.

Use and Utility

The compounds of formula I and II are microtubule-stabilizing agents. They are thus useful in the treatment of a variety of cancers, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds of formula I and II may also inhibit tumor angiogenesis, thereby affecting the growth of tumors. Such anti-angiogenesis properties of the compounds of formula I and II may also be useful in the treatment of certain forms of blindness related to retinal vascularization, arthritis, especially inflammatory arthritis, multiple sclerosis, restinosis and psoriasis.

Compounds of formula I and II may induce or inhibit apoptosis, a physiological cell death process critical for normal development and homeostasis. Alterations of apoptotic pathways contribute to the pathogenesis of a variety of human diseases. Compounds of formula I and II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I and II can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds of formula I and II which exert their effects at the $G_2$-M phase.

The present compounds may exist as multiple optical, geometric, and stereoisomers. Included within the present invention are all such isomers and mixtures thereof in the racemic form.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Methods of Preparation

Compounds of formula I and II are prepared by the following schemes.

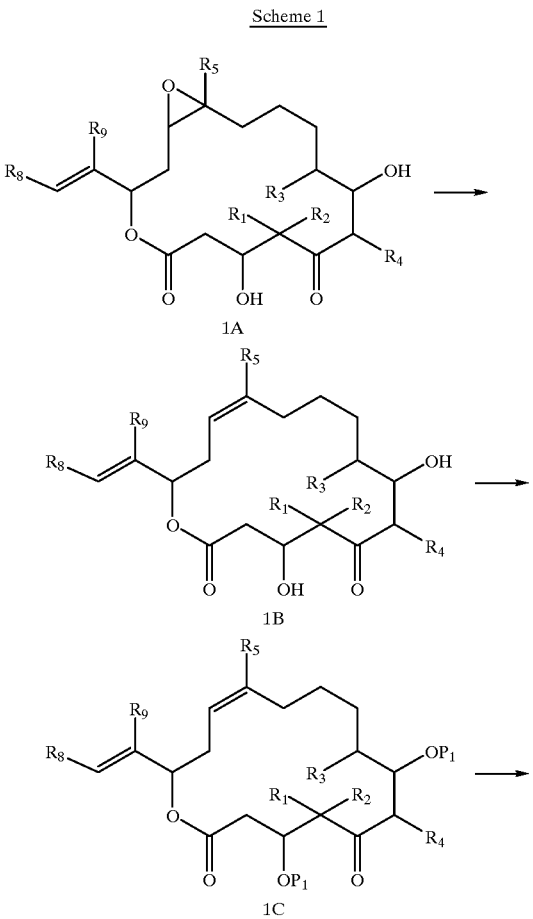

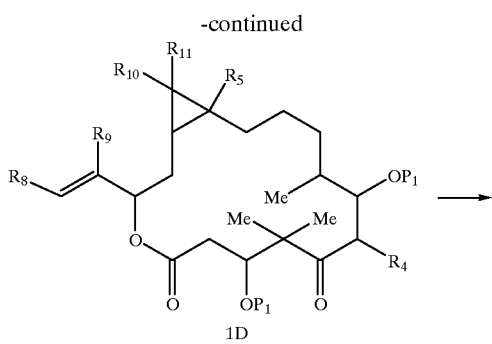

1D

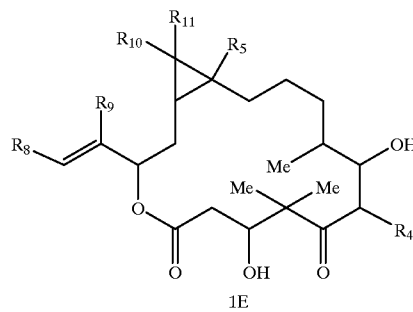

1E

Compounds of formula I can be prepared as outlined in Scheme 1. A compound of formula 1B can be prepared from an epothilone of formula 1A by reduction with a reducing agent such as "reactive titanocene" ($Cp_2TiCl_2/Mg$) or tungsten metal ($WCl_6/n$-BuLi). Optionally, a compound of formula 1C, where $P_1$ is an oxygen protecting group such as triethylsilyl, can be prepared from a compound of formula 1B by methods known in the art. A compound of formula 1D, where $R_{10}$ and $R_{11}$ are H, can be prepared from a compound of formula 1C by addition of a carbene group according to the method of Denmark (Denmark, S. E., et al., *J. Org. Chem.*, (1991) 56, 6974). When $P_1$ is an oxygen protecting group, a deprotection step using, for example when $P_1$ is a triethylsilyl group, hydrogen fluoride in acetonitrile or tetra-n-butylammonium fluoride in THF or trifluoroacetic acid in dichloromethane provides a compound of formula I (1E) where $R_1$, $R_2$, $R_3$, $R_4$ and $R_5$ are defined as described above.

Alternatively, a compound of formula 1B can be converted directly to a compound of formula I (1E) without using oxygen protecting groups (i.e., $P_1$ is H) using the method described above for the conversion of 1C to 1D.

Alternatively, a compound of formula 1B, or its optionally protected form 1C, can be converted to a compound of formula 1D where where Rio and $R_{11}$ are halogen, such as bromine, by treatment with a dihalocarbene which can be generated, for example, by reaction of sodium hydroxide and bromoform. Dehalogenation of a compound of formula 1D can be achieved with a reducing agent such as tri-n-butyltin hydride to give a compound of formula I (1E). If $P_1$ is an oxygen protecting group, a deprotection step using, for example when $P_1$ is a triethylsilyl group, hydrogen fluoride in acetonitrile or tetra-n-butylammonium fluoride in THF or trifluoroacetic acid in dichloromethane provides a compound of formula I (1E) where $R_1$, $R_2$, $R_3$, $R_4$ and $R_5$ are defined as described above.

Other compounds of formula I (i.e., 1E where $R_{10}$ and $R_{11}$ are not H or halo) can be prepared from a compound of formula 1C by reaction of a diazo compound and a transition metal catalyst (See for example: Davies, H. M. L., et al., *J. Org CHEM.*, (1991) 56, 3817, and the methods described in "The Chemistry of the Cyclopropyl Group" Parts 1 and 2, Z. Rappoport, Ed., John Wiley and Sons: New York (1987)).

Scheme 2

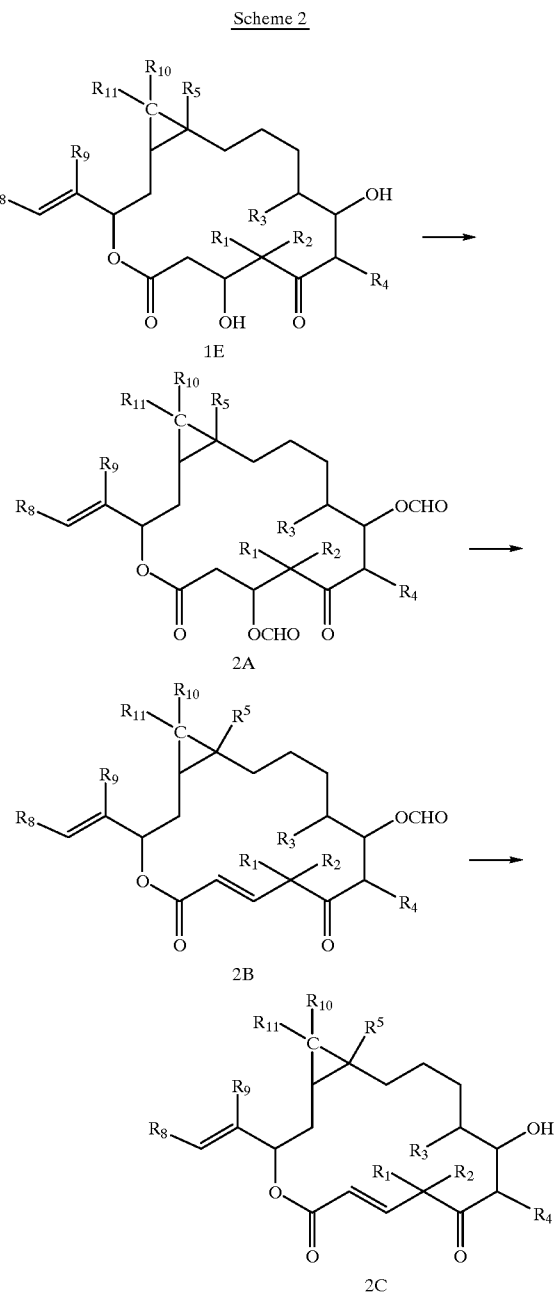

Compounds of formula II can be prepared from a compound of formula IE, where $B_1$ and B2 are hydroxyl groups, as shown in Scheme 2. A compound of formula 2A can be prepared from compounds of formula I by addition of formyl groups using standard conditions such as formic acid, triethylamine, acetic anhydride in dichloromethane. Elimination of a compound of formula 2A using 1,8-diazabicyclo[5.4.0]undec-7-ene in dichloromethane provides a compound of formula 2B. Deprotection of a compound of formula 2B using ammonia in methanol provides a compound of formula II (2C).

The in vitro assessment of biological activity of the compounds of Formula I and II was performed as follows:

In vitro Tubulin Polymerization

Twice cycled (2X) calf brain tubulin was prepared following the procedure of Williams and Lee (see Williams, R. C., Jr., and Lee, J. C. Preparation of tubulin from brain. Methods in Enzymology 85, Pt. D: 376–385, 1982) and stored in liquid nitrogen before use. Quantification of tubulin polymerization potency is accomplished following a modified procedure of Swindell, et al., (see Swindell, C. S., Krauss, N. E., Horwitz, S. B., and Ringel, I. Biologically active taxol analogues with deleted A-ring side chain substituents and variable C-2' configurations. *J. Med. Chem.* 34: 1176–1184, 1991). These modifications, in part, result in the expression of tubulin polymerization potency as an effective concentration for any given compound. For this method, different concentrations of compound in polymerization buffer (0.1M MES, 1mM EGTA, 0.5 mM MgCl2, pH 6.6) are added to tubulin in polymerization buffer at 37° in microcuvette wells of a Beckman (Beckman Instruments) Model DU 7400 UV spectrophotometer. A final microtubule protein concentration of 1.0 mg/ml and compound concentration of generally 2.5, 5.0, and 10 μM are used. Initial slopes of OD change measured every 10 seconds were calculated by the program accompanying the instrument after initial and final times of the linear region encompassing at least 3 time points were manually defined. Under these conditions linear variances were generally <$10^{-6}$, slopes ranged from 0.03 to 0.002 absorbance unit/minute, and maximum absorbance was 0.15 absorbance units. Effective concentration ($EC_{0.01}$) is defined as the interpolated concentration capable of inducing an initial slope of 0.01 OD/minute rate and is calculated using the formula: $EC_{0.01}$= concentration/slope. $EC_{0.01}$ values are expressed as the mean with standard deviation obtained from 3 different concentrations. $EC_{0.01}$ values for the compounds in this invention fall in the range 0.01–1000 μM.

Cytoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," *Mol. Biol. Cell* 3 (Suppl.):184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an $IC_{50}$, which is the drug concentration required to inhibit cell proliferation (i.e. absorbance at 450 nM) to 50% of that of untreated control cells. The $IC_{50}$ values for compounds of this invention fall in the range 0.01–1000 nM.

The following examples illustrate the present invention.

EXAMPLE 1

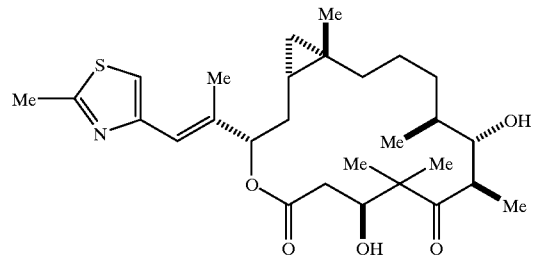

[1S-[1R*,3R*(E),7R*,10S*,11R*,12R*,16R*]]-7,11-Dihydroxy-8,8,10,12,16-pentamethyl-3-[1-methyl-2-(2-methyl-4-thiazolyl)ethenyl]-4-oxabicyclo[14.1.0] heptadecane-5,9-dione A. [4S-[4R*,7S*,8R*,9R*,16R*(E)]]-4,8-Dihydroxy-5,5,7,9,13-pentamethyl-16-[1-methyl-2-(2-methyl-4-thiazolyl) ethenyl]-1-oxa-13(Z)-cyclohexadecene-2,6-dione. [Epothilone D]

To anhydrous THF (5 ml) at −78° C. under argon was added $WCl_6$ (198 mg, 0.5 mmol) followed by nBuLi (0.625 ml of 1.6 M solution in hexanes, 1.0 mmol). The reaction was allowed to warm to room temperature over a 20 min period. An aliquot (0.50 ml, 0.05 mmol) of the tungsten reagent was removed and added to epothilone B (9.0 mg, 0.018 mmol) under argon and the reaction stirred for 15 min then quenched by the addition of saturated $NaHCO_3$ (1 ml). The reaction was extracted with EtOAc (3×1 ml). The combined extracts dried ($Na_2SO_4$), and filtered. The volatiles removed under vacuum. The residue was chromatographed with 35% EtOAc/hexanes to give compound A (7.0 mg, 0.014 mmol) in 80% yield. m/z: 492.3 $(M+H)^+$.

B. [4S-[4R*,7S*,8R*,9R*,16R*(E)]]-4,8-Bistriethylsilyloxy-5,5,7,9,13-pentamethyl-16-p[1-methyl-2-(2-methyl-4-thiazolyl)ethenyl 1-oxa-13(Z)-cyclohexadecene-2,6-dione. [Bis-Triethylsilyl Epothilone D]

To a solution of compound A (30 mg, 0.061 mmol) in anhydrous $CH_2Cl_2$ (1.25 mL) under argon were added N,N-diisopropylethylamine (0.16 mL, 0.92 mmol, 15 eq) followed by triethysilytcheoride (0.10 mL, 0.61 mL, 10 eq). The reaction mixture was stirred for 18 hrs. The reaction mixture was cooled to 0° C. then 2,6-lutidine (0.021 mL, 0.18 mmol, 3 eq) was added followed by triethylsilyltrifluoromethanesulphonate (0.056 mL, 0.2 4 mmol, 4 eq). The reaction was stirred for 0.5 hr then poured into a 1:1 mixture of $H_2O$/saturated $NaHCO_3$ (1 mL) and extracted with $CH_2Cl_2$ ( 3×1 mL). The combined organics were dried ($Na_2SO_4$), filtered, and the volatiles were removed. The residue was chromatographed with 1% $Et_2O/CH_2Cl_2$ to give 35 mg of compound B (80% yield) as a clear glass. m/z: 720.5 $(M+H)^+$.

C. [1S-[1R*,3R*(E),7R*,10S*,11R*,12R*,16R*]]-7,11-Dihydroxy-8,8,10,12,16-pentamethyl-3-(1-methyl-2-(2-methyl-4-thiazolyl)ethenyl]4-oxabicyclo[14.1.0] heptadecane-5,9-dione To a solution of diethylzinc (0.24 mL of 1.0 M in heptane, 0.24 mmol, 5 eq) in 1,2-dichloroethane (1.5 mL) at −15° C. under argon was added chloroiodomethane (0.035 mL, by 0.48 mmol, 10 eq), and the mixture was stirred for 10 mn. A solution of compound B (35 mg, 0.048 mmol) in 1,2-dichloroethane (0.40 mL) was slowly added, and the reaction mixture 25 was stirred for 1.5 hrs. The reaction was quench ed by addition of saturated NH$_4$Cl (1.5 mL) and extracted with CH$_2$Cl$_2$ (3×2 mL). The combined organics were dried (Na$_2$SO$_4$), filtered, and the volatiles removed in vacuo. To the residue was added 15% trifluoroacetic acid/ CH$_2$Cl$_2$ (0.50 mL) and the reaction stirred for 15 min. The volatiles were removed under a stream of air and the residue was chromatographed with 70% EtOAc/hexanes to give 2.2 mg of title compound (10% yield- two steps) as a white film; m/z: 506.3 (M+H)$^+$.

Alternatively, sodium hydroxide (0.3 ml of 50% solution in H$_2$O) was added to compound 1B (109 mg, 0.15 mmol), PhCH$_2$(CH$_3$CH$_2$)$_3$NCl (0.7 mg, 0.002 mmol), and EtOH (0.03ml) in CHBr$_3$ (1.0 ml). The resulting mixture was heated at 40° C. for 2 hr. The brown reaction mixture was diluted with H$_2$O (30 ml), extracted with CH$_2$Cl$_2$ (3×30 ml), dried over Na$_2$SO$_4$, concentrated and purified by flash chromatography (stepwise gradient: 5 to 25% Et2O/ hexanes) to afford a dibromocyclopropane intermediate as a light brown oil (40mg, 30% yield). (M+H)$^+$892.3

Bu$_3$SnH (3.4 mmol, 0.91 ml) was added to the dibromocyclopropane intermediate (0.34 mmol, 305 mg) and 2,2-azobisisobutyronitrile (0.034 mmol, 6 mg) in hexanes (7.0 ml). The reaction mixture was heated at 70° C. for 5 hr. The reaction was concentrated and purified by flash chromatography (stepwise gradient: hexanes to 20%Et$_2$O/ hexanes) to afford a reduced cyclopropane intermediate as a clear film (228 mg, 91%). (M+H)$^+$734.7.

The preceding cyclopropane intermediate(0.31 mmol, 228 mg) was dissolved in CF$_3$CO$_2$H/CH$_2$Cl$_2$ (20% solution by volume, 10 ml) and stirred at −15° C. for 1.5 hr. The reaction mixture was concentrated and purified by flash chromatography (70%EtoAc/Hexanes) to afford the title compound as a clear oil (111 mg, 71%). (M+H)$^+$506.3. $^1$H NMR (CDCl$_3$, 400 MHz) d 7.04 (s, 1H), 6.64 (s, 1H), 5.16 (dd, J=8.0, 3.4 Hz, 1H), 4.17 (dd, J=9.5, 2.8 Hz, 1H), 3.79–3.83 (m, 1H), 3.23 (dq, J=6.7, 4.5 Hz, 1H), 2.79 (s, 3H), 2.52 (dd, J=15.1, 9.7 Hz, 1H), 2.41 (dd, J=15.2, 2.9 Hz, 1H), 1.98–2.02 (m, 1H), 2.00 (s, 3H), 1.63–1.73 (m, 1H), 1.40–1.58 (m, 5H), 1.36 (s, 3H), 1.20–1.3 (m, 1H), 1.11–1.17 (m, 1H), 1.15 (d, J=6.8 Hz, 3H), 1.08 (s, 3H), 0.96 (d, J=7.0 Hz, 3H), 0.94 (s, 3H), 0.40–0.54 (m, 1H), 0.37 (dd, J=8.8, 4.1 Hz, 1H), −0.14-(−0.10) (m, 1H).

EXAMPLE 2

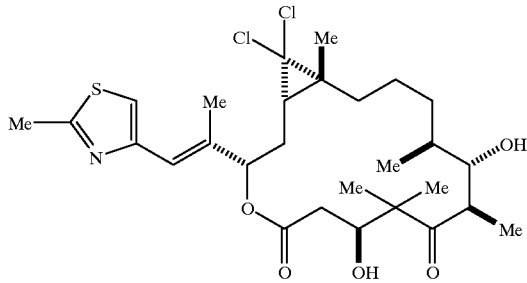

[1S-[1R*,3R*(E),7R*,10S*,11R*,12R*,16S*]]-17- Dichloro-7,11-dihydroxy-8,8,10,12,16-pentamethyl-3-[1- methyl-2-(2-methyl-4-thiazolyl)ethenyl]-4-oxabicyclo [14.1.0]heptadecane-5,9-dione A. [1S-[1R*,3R*(E),7R*,10S*,11R*,12R*,16S*]]-17- Dichloro-7,11-bistriethylsilyloxy-8,8,10,12,16- pentamethyl-3-[1-methyl-2-(2-methyl-4-thiazolyl)ethenyl]- 4-oxabicyclo [14.1.0]heptadecane-5,9-dione Sodium hydroxide (1.7 ml of 50% solution in H$_2$O) was added to compound 1B (1.04 g, 1.44 mmol), benzyltriethylammonium chloride (7 mg, 0.03 mmol), and EtOH (0.06ml) in CHCl$_3$ (11 ml). The reaction mixture was stirred at room temperature for 2 hr. The brown reaction mixture was diluted with H$_2$O(60 ml), extracted with CH$_2$Cl$_2$ (3×50 ml), dried over Na$_2$SO$_4$, concentrated and purified by flash chromatography (stepwise gradient: hexanes to 8% EtOAc/ hexanes) to afford compound A as light brown oil (361 mg, 31% yield). (M+H)$^+$804.5

B. [1S-[1R*,3R*(E),7R*,10S*,11R*,12R*,16S*]]-17- Dichloro-7,11-dihydroxy-8,8,10,12,16-pentamethyl-3-[1- methyl-2-(2-methyl-4-thiazolyl)ethenyl]-4-oxabicyclo [14.1.0]heptadecane-5,9-dione Compound A (0.27 mmol, 220 mg) in CF$_3$CO$_2$H/CH$_2$Cl$_2$ (20% solution by volume, 10 ml) was stirred at −15° C. for 1.5 hr. The reaction was concentrated and purified by flash chromatography (70%EtOAc/Hexanes) to afford the title compound as a light brown oil (126 mg, 81%). (M+H)$^+$ 574.4

EXAMPLE 3

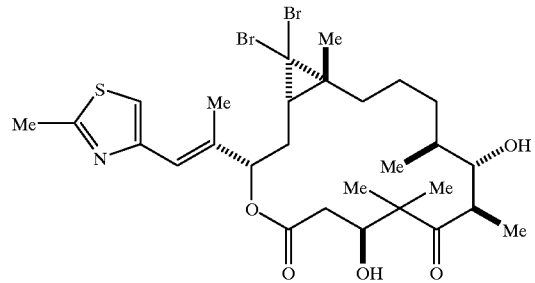

[1S-[1R*,3R*(E),7R*,10S*,11R*,12R*,16S*]]-17- Dibromo-7,11-dihydroxy-8,8,10,12,16-pentamethyl-3-[1- methyl-2-(2-methyl-4-thiazolyl)ethenyl]-4-oxabicyclo [14.1.0]heptadecane-5,9-dione A. [1S-[1R*,3R*(E),7R*,10S*,11R*,12R*,16S*]]-17- Dibromo-7,11-bistriethylsilyloxy-8,8,10,12,16- pentamethyl-3-[1-methyl-2-(2-methyl-4-thiazolyl)ethenyl]- 4-oxabicyclo[14.1.0]heptadecane-5,9-dione Sodium hydroxide (0.3 ml of 50% solution in H$_2$O) was added to compound 1B (109 mg, 0.15 mmol), benzyltriethylammonium chloride (0.7 mg, 0.002 mmol), and EtOH (0.03ml) in CHBr$_3$ (1.0 ml). The resulting mixture was heated at 40° C. for 2 hr. The brown reaction mixture was diluted with H$_2$O (30 ml), extracted with CH$_2$Cl$_2$ (3×30 ml), dried over Na$_2$SO$_4$. The organic extracts were concentrated and the residue was purified by flash chromatography (stepwise gradient: 5 to 25% Et2O/hexanes) to afford compound A as light brown oil (40mg, 30% yield). (M+H)$^+$892.3

B. [1S-[1R*,3R*(E),7R*,10S*,11R*,12R*,16S*]]-17- Dibromo-7,11-dihydroxy-8,8,10,12,16-pentamethyl-3-[1- methyl-2-(2-methyl-4-thiazolyl)ethenyl]-4-oxabicyclo [14.1.0]heptadecane-5,9-dione Compound A (0.0045 mmol, 4 mg) in CF$_3$CO$_2$H/CH$_2$Cl$_2$ (15% solution by volume, 10 ml) was stirred at −15° C. for 1.5 hr. The reaction mixture was concentrated and purified by flash chromatography (70%EtoAc/Hexanes) to afford the title compound as a clear oil (2 mg, 66%). (M=H)$^+$664.2

EXAMPLE 4

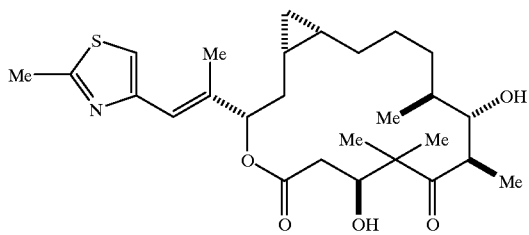

[1S-[1R*,3R*(E),7R*,10S*,11R*,12R*,16R*]]-7,11-Dihydroxy-8,8,10,12-tetramethyl-3-[1-methyl-2-(2-methyl-4-thiazolyl)ethenyl]-4-oxabicyclo[14.1.0]heptadecane-5,9-dione A. [4S-[4R*,7S*,8R*,9R*,16R*(E)]]-4,8-Dihydroxy-5,5,7,9-tetramethyl-16-[1-methyl-2-(2-methyl-4-thiazolyl)ethenyl]-1-oxa-13(Z)-cyclohexadecene-2,6-dione. [Epothilone C]

To a two-necked flask was added chopped pieces of magnesium turnings (24 mg, 1.0 mmol). The flask was flame-dried under vacuum and cooled under argon. Bis(cyclopentadienyl)titanium dichloride (250 mg, 1.0 mmol) was added followed by anhydrous THF (5 mL). The stirring suspension was evacuated with low vacuum, and the reaction flask was refilled with argon. The red suspension became dark, turning a homogeneous deep green after 1.5 hr with nearly all the magnesium metal being consumed. An aliquot (3.5 mL, 0.70 mmol, 3.5 eq) was removed and cooled to −78° C. under argon. To this solution was added epothilone A (99 mg, 0.20 mmol, 1.0 eq). The reaction mixture was warmed to room temperature and stirred for 15 min. The volatiles were removed in vacuo and the residue was chromatographed two times on silica (25 g), eluting with 35% EtOAc/hexanes to give 76 mg (80%) of compound A as a pale yellow viscous oil.

B. [4S-[4R*,7S*,8R*,9R*,16R*(E)]]-4,8-Bis(t-butyldimethylsilyloxy)-5,5,7,9-tetramethyl-16-[1-methyl-2-(2-methyl4-thiazolyl)ethenyl] -1-oxa-13(Z)-cyclohexadecene-2,6-dione tert-Butyldimethylsilyl trifluoromethanesulfonate (0.1 ml, 0.43 mmol) was added to compound A (76 mg, 0.16 mmol) and 2,6-lutidine (0.074 ml, 0.64 mmol) in $CH_2Cl_2$ (2.5 ml). The reaction mixture was stirred at −20° C. for 30 min, and quenched with $H_2O$ (10 ml). The reaction mixture was extracted with $CH_2Cl_2$ (2×10 ml), dried over $Na_2SO_4$, concentrated and puriified by flash chromatography (10% EtoAc/Hexanes) to afford compound B as a white solid (89mg, 79%). $(M+H)^+706.2$ C. [1S-[1R*,3R*(E),7R*,10S*,11R*,12R*,16S*]]-17-Dibromo-7,11-bis(t-butyldimethylsilyloxy)-8,8,10,12-tetramethyl-3-[1-methyl-2-(2-methyl-4-thiazolyl)ethenyl]-4-oxabicyclo[14.1.0]heptadecane-5,9-dione To a solution of compound B (85 mg, 0.12 mmol) in $CHBr_3$ (1.0 ml) was added benzyltriethylammonium chloride (3.0 mg, 0.013 mmol), EtOH (0.010 mL), and then 50% NaOH (aq) (0.17 ml, 3.2 mmol). The reaction mixture was vigorously stirred at 50° C. for 48 hr, cooled to room temperature, and then chromatographed directly (7% EtOAc/hexanes) to give compound C (15 mg, 14%) as a pale yellow solid. $(M+H)^+878$ D. [1S-[1R*,3R*(E),7R*,10S*,11R*,12R*,16R*]]-7,11-Bis(t-butyldimethylsilyloxy)-8,8,10,12-tetramethyl-3-[1-methyl-2-(2-methyl-4-thiazolyl)ethenyl]-4-oxabicyclo[14.1.0]heptadecane-5,9-dione To a solution of compound C (11.5 mg, 0.013 mmol) in hexanes (0.20 ml) was added tributyltin hydride (0.021 ml, 0.080 mmol) followed by 2,2-* azobisisobutyronitrile (0.0013 mmol, <1 mg). The reaction mixture was heated at reflux for 2 hr. The reaction mixture was cooled to room temperature. The volatiles removed under a stream of air, and the residue was chromatographed (0 to 8% EtOAc/hexanes) to give compound D (7.2 mg, 77%) as a clear oil. $(M+H)^+720$ E. [1S-[1R*,3R*(E),7R*,10S*,11R*,12R*,16R*]]-7,11-Dihydroxy-8,8,10,12-tetramethyl-3-[1-methyl-2-(2-methyl-4-thiazolyl)ethenyl]-4-oxabicyclo [14.1.0]heptadecane-5,9-dione To compound D (7.1 mg, 0.0099 mmol) at −15° C. was added 20% trifluoroacetic acid/$CH_2Cl_2$ (0.30 mL). The reaction was warmed to 0° C. and stirred for 2 hr. The volatiles were removed under a stream of air, and the residue was chromatographed with 40% EtOAc/hexanes to give the title compound (4.3 mg, 89%) as a clear, viscous oil. $(M+H)^+492$. $^1H$ NMR ($CDCl_3$, 400 MHz) 6.93 (s, 1H), 6.54 (s, 1H), 5.25 (dd, J=9.2, 3.6 Hz, 1H), 4.07–4.11 (m, 1H), 3.83–3.87 (m, 1H), 3.15–3.20 (m, 1H), 2.68 (s, 3H), 2.51 (dd, J=15.0, 9.2 Hz, 1H), 2.44 (dd, J=15.0, 3.4 Hz, 1H), 2.01–2.07 (m, 1H), 2.03 (s, 3H), 1.67–1.71 (m, 1H), 1.44–1.53 (m, 3H), 1.37–1.45 (m, 1H), 1.3 (s, 3H), 1.16–1.30 (m, 2H), 1.14 (d, J=7.0 Hz, 3H), 1.13 (s, 3H), 1.05–1.13 (m, 1H), 0.97 (d, J=7.0 Hz, 3H), 0.57–0.72 (m, 3H), −0.33 (dd, J=9.7, 5.3 Hz, 1H).

EXAMPLE 5

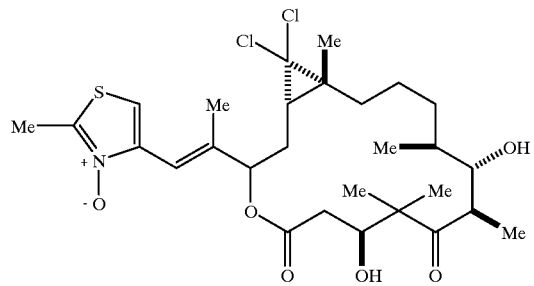

[1S-[1R*,3R*(E),7R*,10S*,11R*,12R*,16S*]]-17-Dichloro-7,11-dihydroxy-8,8,10,12,16-pentamethyl-3-[1-methyl-2-(2-methyl-3-oxo-4-thiazolyl)ethenyl]-4-oxabicyclo[14.1.0]heptadecane-5,9-dione m-Chloroperoxybenzoic acid (1.5 mmol, 260 mg) was added to compound 2B (303 mg, 0.53 mmol) in $CH_2Cl_2$ (12 ml). The reaction mixture was stirred at room temperature for 5 hr. The reaction mixture was washed with NaHCOa (2×50 ml), $Na_2SO_3$ (2×50 ml of 50mg/ml solution), $H_2O$ (2×50 ml), and then dried over $Na_2SO_4$. The organic extracts were concentrated and the residue was purified using HPLC (500×30 mm YMC ODS column, 15 to 100% solvent B over 50 min; solvent A:10:90, $H_2O$:$CH_3CN$; solvent B: 90:10, $H_2O$:$CH_3CN$; flow rate: 20 ml/min) to afford title compound, as a white solid (91 mg, 27%). $(M+H)^+590.2$

EXAMPLE 6

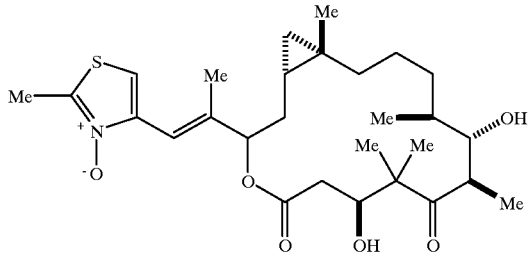

[1S-[1R*,3R*(E),7R*,10S*,11R*,12R*,16R*]]-7,11l-Dihydroxy-8,8,10,12,16-pentamethyl-3-[1-methyl-2-(2-methyl-3-oxo-4-thiazolyl)ethenyl]-4-oxabicyclo[14.1.0]heptadecane-5,9-dione m-Chloroperoxybenzoic acid (0.013 mmol, 2.2 mg) was added to compound 1C (3 mg, 0.006 mmol) in $CH_2Cl_2$ (0.15 ml). The reaction mixture was stirred at room temperature for 2.5 hr. The reaction mixture was concentrated and purified by flash chromatography (2%MeOH/$CHCl_3$) to afford the title compound (1.0 mg, 32%) as a white solid. $(M+H)^+522.3$.

What is claimed is:

1. A compound of the formula

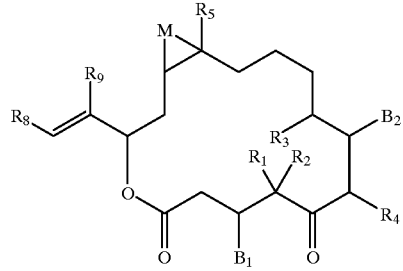

I

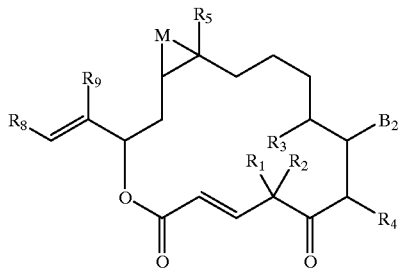

II wherein:
- $B_1$ and $B_2$ are selected from the group consisting of H, or $OR_6$;
- $R_1$, $R_2$, $R_3$, and R4, are selected from H, lower alkyl;
- $R_5$ is selected from the group consisting of H, alkyl, substituted alkyl;
- $R_8$ is heterocyclo;
- $R_9$ is hydrogen or lower alkyl;
- $R_6$ is hydrogen or alkyl;
- M is $CR_{10}R_{11}$;
- $R_{10}$ and $R_{11}$ are selected from the group consisting of H, halogen, alkyl, substituted alkyl, aryl, substituted aryl, cycloalkyl, heterocyclo, $R_{12}C=O$, $R_{13}OC=O$, $R_{14}NHC=O$, hydroxy, O-alkyl or O-substituted alkyl, $NR_{15}R_{16}$;
- $R_{12}$, $R_{13}$, $R_{14}$, $R_{15}$, $R_{17}$, $R_{18}$ and $R_{19}$ are selected from the group consisting of H, alkyl, substituted alkyl, aryl, acyl or substituted aryl;
- $R_{16}$ is selected from the group consisting of H, alkyl, substituted alkyl, aryl, substituted aryl, cycloalkyl, heterocyclo, $R_{17}C=O$, $R_{18}OC=O$, $R_{19}SO_2$, hydroxy, O-alkyl, or O-substituted alkyl:

and any salts, solvates or hydrates thereof.

2. The compound of claim 1 wherein $R_8$ is a 2-methyl-4-thiazolyl.

3. The compound of claim 2 wherein $R_{10}$ and $R_{11}$ are halogen.

4. The compound of claim 3 wherein $R_{10}$ and $R_{11}$ are chlorine or bromine.

5. A compound of the formulas

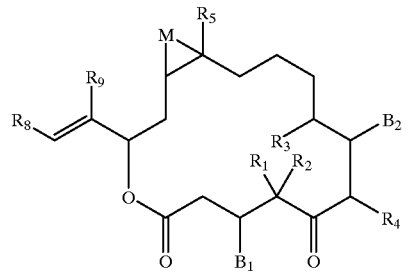

I

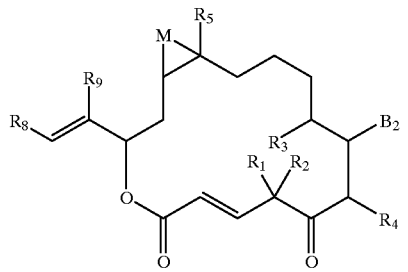

II wherein:
- $B_1$ and $B_2$ are selected from the group consisting of H, or $OR_6$;
- $R_1$, $R_2$, $R_3$, and $R_4$ are selected from H, lower alkyl;
- $R_5$ is selected from the group consisting of H, alkyl, substituted alkyl;
- $R_8$ is heterocyclo;
- $R_9$ is hydrogen or lower alkyl;
- $R_6$ is hydrogen or alkyl;
- M is $CH_2$;

and any salts, solvates or hydrates thereof.

6. The compound of the formula:

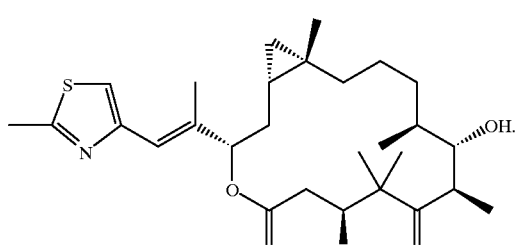

7. The compound of the formula:

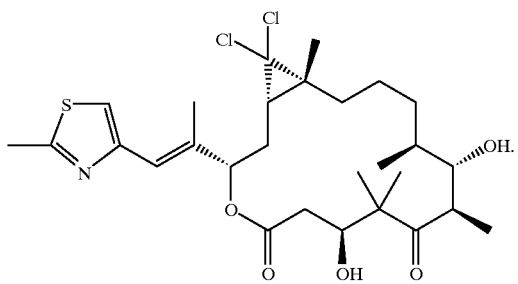

8. The compound of the formula:

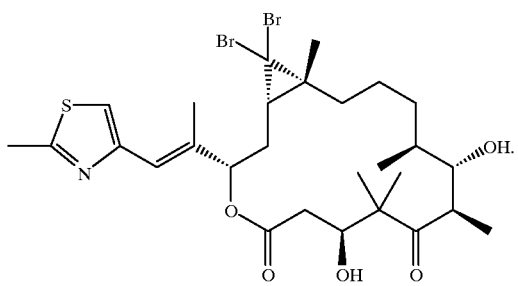

9. The compound of the formula:

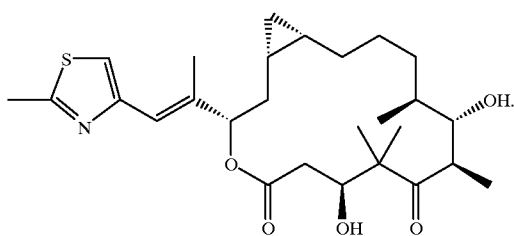

10. The compound of the formula:

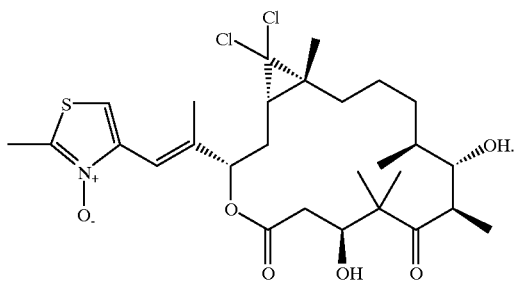

11. The compound of the formula:

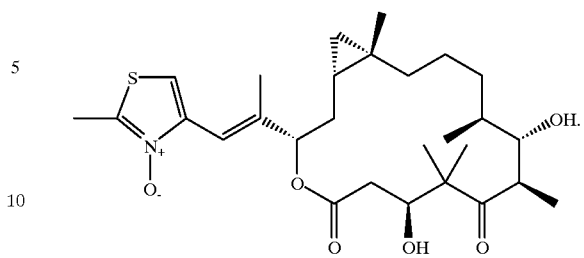

12. A pharmaceutical composition comprising a compound of claim 1 and a pharmaceutically acceptable vehicle or diluent.

13. A pharmaceutical composition comprising a compound of claim 2 and a pharmaceutically acceptable vehicle or diluent.

14. A pharmaceutical composition comprising a compound of claim 3 and a pharmaceutically acceptable vehicle or diluent.

15. A pharmaceutical composition comprising a compound of claim 4 and a pharmaceutically acceptable vehicle or diluent.

16. A pharmaceutical composition comprising a compound of claim 5 and a pharmaceutically acceptable vehicle or diluent.

17. A pharmaceutical composition comprising a compound of claim 6 and a pharmaceutically acceptable vehicle or diluent.

18. A pharmaceutical composition comprising the compound of claim 7 and a pharmaceutically acceptable vehicle or diluent.

19. A pharmaceutical composition comprising the compound of claim 8 and a pharmaceutically acceptable vehicle or diluent.

20. A pharmaceutical composition comprising the compound of claim 9 and a pharmaceutically acceptable vehicle or diluent.

21. A pharmaceutical composition comprising the compound of claim 10 and a pharmaceutically acceptable vehicle or diluent.

22. A pharmaceutical composition comprising the compound of claim 11 and a pharmaceutically acceptable vehicle or diluent.

* * * * *

UNITED STATES PATENT AND TRADEMARK OFFICE
Certificate

Patent No. 6,380,395 B1                                    Patented: April 30, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gregory D. Vite, Titusville, NJ (US); Soong-Hoon Kim, Lawrenceville, NJ (US); Gerhard Hofle, Braunschweig (DE); and James A. Johnson, Lawrenceville, NJ (US).

Signed and Sealed this Seventeenth Day of June 2008.

SHAOJIA JIANG
*Supervisory Patent Examiner*
Art Unit 1623